United States Patent [19]

Sudate et al.

[11] Patent Number: 5,861,152
[45] Date of Patent: Jan. 19, 1999

[54] *HUMICOLA GRISEA* VAR. *GRISEA* ANTAGONISTIC AGAINST SNOW-MOLD PATHOGENIC FUNGI, AND SNOW-MOLD CONTROL AGENT AND METHOD USING THE SAME

[75] Inventors: Yasuhiro Sudate, Tagata-gun; Takanori Fujiwara, Hachioji, both of Japan

[73] Assignees: Asahi Kasei Kogyo Kabushiki Kaisha, Osaka; Kabushiki Kaisha Ishikatsu Exterior Inc., Tokyo, both of Japan

[21] Appl. No.: 875,595

[22] PCT Filed: Mar. 18, 1996

[86] PCT No.: PCT/JP95/00702

§ 371 Date: Jul. 31, 1997

§ 102(e) Date: Jul. 31, 1997

[87] PCT Pub. No.: WO96/28977

PCT Pub. Date: Sep. 26, 1996

[30] Foreign Application Priority Data

Mar. 20, 1995 [JP] Japan ................... 7-060550

[51] Int. Cl.$^6$ ............... A01N 63/00; C12N 1/14
[52] U.S. Cl. ............ 424/935; 435/254.1; 435/911
[58] Field of Search .............. 435/254.1; 424/93.5

[56] References Cited

U.S. PATENT DOCUMENTS 3,428,526  2/1969  Sigg et al. .................. 195/80
4,900,348  2/1990  Hoitink ........................ 71/6
5,418,165  5/1995  McBeath ................... 435/256.7
5,422,107  6/1995  Kubota ...................... 424/93.5

FOREIGN PATENT DOCUMENTS

| 5-236939 | 9/1993 | Japan . |
| 5-286819 | 11/1993 | Japan . |
| 6-192028 | 7/1994 | Japan . |
| 6-211616 | 8/1994 | Japan . |
| 7-25716 | 1/1995 | Japan . |
| 7-289242 | 11/1995 | Japan . |

OTHER PUBLICATIONS

J. Draw Smith et al., "Acremonium boreal n.sp., a sclerotial, low-temperature-tolerant, snow mold antagonist", *Canadian Journal of Botany*, vol. 57, 1979, pp. 2122–2139.

*Primary Examiner*—Sandra E. Saucier
*Assistant Examiner*—Vera Afremova
*Attorney, Agent, or Firm*—Young & Thompson

[57] ABSTRACT

An agent for controlling snow blight disease damage, which comprises a filamentous fungus of the genus Humicola exhibiting an antagonistic activity against the pathogenic fungi of snow blight diseases but harmless to animals and plants or which comprises a microbial product containing such filamentous fungus, as well as a method for controlling snow blight diseases using such control agent which allows an efficient control of snow blight. In particular the fungus is *Humicola grisea* var. *grisea* FERM BP-5452.

11 Claims, No Drawings

HUMICOLA GRISEA VAR. GRISEA ANTAGONISTIC AGAINST SNOW-MOLD PATHOGENIC FUNGI, AND SNOW-MOLD CONTROL AGENT AND METHOD USING THE SAME

This application is a 371 of PCT/JP96/00702 filed Mar. 18, 1996.

FIELD OF THE INVENTION

The present invention relates to filamentous fungi of the genus Humicola which have antagonistic activity against pathogenic fungi of snow blight (i.e. snow mold) diseases but are harmless to animals and plants and capable of suppressing snow blights including Typhula snow blight (*Typhula incarnata*), Typhula snow blight (*Typhula ishikariensis*), Fusarium snow blight (*Fusarium nivale* f. sp. *graminicola*), Pythium snow blight and Sclerotinia as well as other plant diseases, on the one hand, and to an agent and method for controlling snow blights using such filamentous fungi, on the other hand.

BACKGROUND OF THE INVENTION

Snow blights bring about a significant disease damage onto gramineous plants, wheat, barley, oat and leguminous plants in cold snowy districts and are identified in accordance with each corresponding pathogenic fungus by the denotations, such as Typhula snow blight (*Typhula incarnate*), Typhula snow blight (*Typhula ishikariensis*), Fusarium snow blight (*Fusarium nivale* f. sp. *graminicola*), Pythium snow blight and Sclerotinia. These diseases are characterized by causing damages on gramineous plants, wheat, barley, oat and leguminous plants under the laid snow, whereby the damaged plant may, after the thawing of snow, be dead by rotting of the foliage and be blighted upon drying or may suffer from retarded growth. Such a damage due to snow blight diseases is well known, especially, for lawn grass. Since the damage by snow blight is caused on plants, especially gramineous plants, beneath the laid snow, a prophylaxis or therapy of snow blight diseases is difficult to realize. There have hitherto been used for controlling snow blights agents based on organic copper compounds, such as those containing, for example, copper 8-hydroxyquinolate, as the effective component; mepronyls containing 3'-isopropoxy-2-methylbenzanilide as the effective component; and agents based on hydroxyisoxazole, such as those containing potassium 3-hydroxy-5-methylisoxazole as the effective component.

These conventional controlling agents are usually applied to the ground twice or thrice before continuous snow coverage has been settled over the ground. Here, a problem of environmental pollution may be provoked by an accidental flooding off or elution of the controlling agent by, for example, rain fall, into watering canals. In addition, so-called acquisition of resistance against the controlling agent may occur also in the pathogenic fungi of snow blights, bringing about a problem in the effectiveness of these controlling agents. Under these circumstances, attempts have been made for utilizig antaginistic reactions (competition, antibiosis and parasitism) between microbes which may be harmonic to ecosystem, by sorting out pertinent microbes. For such microbes, there have been disclosed those in the genus of Acremonium (Canadian Journal of Botany, 57(20), 2122–2139), *Trichoderma haldianum* (Japanese Patent Application Kokai Hei-6-192028), *Typhula acoryzae* (Japanese Patent Application Kokai Hei-5-286819); and those in the genus of Pseudomonas (Japanese Patent Application Kokais Hei-6-211616, Hei-7-25716 and Hei-7-289242). However, it is difficult to sort out an antagonistic microbe active to all the above-mentioned five pathogenic fungi of snow blights and, thus, only a report has hitherto been given for a strain in the genus of Trichoderma (U.S. Pat. No. 5,418,615) for such a microbe. On the other hand, microbes in the genus Humicola are known to grow in mild and high temperature regions above 25° C.

SUMMARY OF THE INVENTION

The inventors have conducted sound researches for preventing snow blight diseases by utilizing microbes. In the course of the researches, the inventors attempted to sort out microbes exhibiting antagonism against the pathogenic fungi of snow blight diseases, in order to find out microbes effective for controlling snow blight diseases. For this purpose, sample earths were collected from various districts, from which microbes were isolated in order to examine for their activities on suppressing or preventing snow blights. The isolated microbes were examined by subjecting it to dual culture with each respective pathogenic fungus at a lower temperature, whereby filamentous fungi of the genus Humicola each capable of suppressing growth of the pathogenic fungi of snow blights were sorted out and found that they can suppress pronouncedly snow blights and other phytopathies even in the open field and, in addition, they are harmless to animals and plants, whereby the present invention has been completed.

Thus, the present invention relates, in one aspect thereof, to filamentous fungi that belong to the genus Humicola and are antagonistic against the pathogenic fungi of snow blights but harmless to animals and plants and, in another aspect thereof, to an agent for controlling snow blights using such filamentous fungi and, in a further aspect thereof, to a method for controlling snow blights characterized by the use of such filamentous fungi.

DESCRIPTION OF THE INVENTION

As the filamentous fungus exhibiting antagonism against the pathogenic fungi of snow blights according to the present invention, one which was identified by the inventors and which belongs to the genus Humicola as well as cultivation products thereof can be employed.

In the method for controlling snow blights, the above-mentioned filamentous fungi of the genus Humicola that exhibit antagonism against the pathogenic fungi of snow blights may desirably be applied onto the ground usually in a dosage of 1,000,000 CFU (Colony Forming Unit) or higher, preferably 1,500,000 CFU or higher, and most preferably 7,500,000 or higher, as the cell amount of the filamentous fungus, by spraying or scattering. While there is no special upper limit of dosage, the practical dosage may be determined appropriately taking into account of economy, workability and so on, and a dosage of, for example, $5 \times 10^{11}$ CFU per 1 $m^2$ of the ground as the cell amount or 500 g of the microbial product mixture per 1 $m^2$ of the ground as the product weight, may be exemplified.

The agent for controlling snow blights according to the present invention (denoted hereinafter as "microbial product for controlling snow blights") is characterized by a content of filamentous fungus or fungi of the genus Humicola exhibiting an antagonism against the pathogenic fungi of snow blights but harmless to animals and plants. The microbial product for controlling snow blights may preferably contain the microbial cells of at least 150,000 CFU per 1 gram of the product with a moisture content of 30% or less.

For the filamentous fungi to be incorporated according to the present invention, no special limitation is given so long as they belong to the genus Humicola and exhibit antagonism against the pathogenic fungi of snow blights and are harmless to animals and do not impart any morbid damage to the objective plants to be protected, especially gramineous plants, wheat, barley, oat and leguminous plants. Such filamentous fungi as psychrophylic fungi with an optimum temperature for the growth at a lower temperature, for example, 18° C. or lower and those which can grow even at 0° C. beneath the laid snow or which exhibit high ability of settling on earths are preferred.

As the pathogenic fungi of snow blights, there may be enumerated fungi which are pathogenic to, for example, Typhula snow blight (*Typhula incarnata*), Typhula snow blight (*Typhula ishikariensis*), Sclerotinia snow blight (*Sclerotinia borealis* and *Myriosclerotinia borealis*), Fusarium snow blight (*Fusarium nivale*) and Pythium snow blight (*Pythium paddicum, Pythium iwayamai, Pythium horinouchiensis* and *Pythium graminicolum*). The lower temperature as expressed herein does mean such a temperature that is encountered under the laid snow or upon the thawing of the laid snow and may be exemplified by 0°–15° C., in particular 3°–7° C.

The filamentous fungi to be incorporated according to the present invention are available by carrying out a dual culture of various fungi with the pathogenic fungi of snow blights at a low temperature and sorting out such a filamentous fungus of the genus Humicola that exhibits an ability for suppressing growth of the pathogenic fungi of snow blights. Examples of such fungi include *Humicola alopallonella, Humicola fuscoatra, Humicola grisea* and *Himicola grisea* var. *thermoidea*.

Furthermore, *Humicola grisea* var. *grisea* M6834 strain, which was discovered by the inventors, is preferable. The mycological properties of this filamentous fungus are as given below.

Morphological Features under Microscope

No perfect stage is formed. The hypha is slightly brownish and the wall is smooth with a width of 2.5–5 μm. The mode of formation of conidium is in two types, i.e. aleuro and phialo types. The aleuro type conidium is dark brown in the color and appears usually in a spherical form having a smooth surface with occasional deformation into subspherical, ellipsoidal and irregular forms. The size thereof is in the range of 12–17 μm. There is no germ pore. It is formed terminally or intermediately and in general singularly, though formation of chained 2- or 3-conidia may occasionally occurs. The conidiophore of the aleuro type extends up to 90 μm with a width of 2.5–5 μm with occasional swelling at the upper part.

The phialo type conidium has an oval form of smooth surface with a length of 2.5–3.0 μm and a width of 2.0–2.5 μm, occurred in a chain. The phialo type conidiophore extends up to 40 μm with a width of 2.0–2.5 μm in a form of colorless cylinder or flask of smooth surface.

Growth State in Culture Media (1) Potato Glucose Agar Medium (PDA)

On cultivating at 25° C. for 7 days, the growth of colony is prompt and reaches a diameter of 45–48 cm with a thick downy surface with 8–10 grooves extending slightly radially and has a complete periphery. The color of the colony is white to greyish green (ICI). The surface of the colony is black in the color. No leaching liquid nor soluble pigment is produced. At 37° C., no growth occurs.

(2) Oatmeal Agar Medium (OA)

On cultivating at 25° C. for 7 days, the growth of colony is prompt and reaches a diameter of 46–48 cm with a downy surface composed of thinly formed white aerial hyphae. The lower portion of the aerial hypha is greyish green (29C, D4) in the color. The circumference of the colony is formed into a complete periphery. On the rear face of the colony, radial zones of grey and greyish green (30B, C4) are interveningly extend radially. No leaching liquid nor soluble pigment is produced. No growth occurs at 37° C.

(3) Malt Extract Agar Medium (MEA)

On cultivating at 25° C. for 7 days, the growth of colony is prompt and reaches a diameter of 50–53 cm with a thick velveteen to somewhat downy surface and thin peripheral zone. The surface of the colony is white. The rear face of the colony is pale orange (5A4) to brownish orange (5C6) with a central portion of purplish orange (14E4). No leaching liquid nor soluble pigment is produced. No growth occurs at 37° C.

Physiological Properties

When cultivated in potato-glucose liquid medium, the pH range permitting growth thereof is 3.0–11.5 with an optimum pH range for the growth being 4.0–8.0. When cultivated in potato-glucose agar medium, the temperature range permitting growth thereof is 3°–34° C. with an optimum temperature range for the growth being 11°–30° C.

Identification

The strain M6834 belongs to Deuteromycotina, because of (1) lack of formation of perfect stage, (2) presence of a septum in the hypha, (3) lack of formation of zoospore with flagellum and (4) occurrence of formation of conidium. It belongs to genus Humicola, because of that the hypha and the conidium are brown in the color, that the conidium has no germ spore and that the hypha has a smooth surface. While fungi of genus Gilmaniella exhibit similar features, a discrimination can be achieved on the bases that the hypha has a rough surface, that a germ pore can be recognized clearly at the top of the conidium and that a developed state of the conidiophore can be seen well.

At present, 6–7 species have been found in the genus Humicola. The features that the aleuro-conidium has a spherical form with a size of 12–17 μm, that phialoconidia are formed and that the growth is prohibited at 37° C. are in better coincidence with *Humicola grisea* var. *grisea*. As resembling species, there are *Humicola fuscoatra* and *Humicola grisea* var. *thermoidea*. Here, discrimination can be achieved by that the *aleuroconidia* have sizes below 10 μm and that the color is somewhat lighter as compared with *Humicola grisea* var. *grisea*. From the above reasens, the M6834 strain was identified as *Humicola grisea* var. *grisea*. This strain of fungus has been deposited with the National Institute of Bioscience and Human-Technology Agency of Industrial Science and Technology, Japan as *Humicola grisea* var. *grisea* M6834 on Mar. 3, 1995 under an accession No. FERM BP-5452.

As will be described later, this fungus strain is harmless to animals and plants and exhibits high antagonism against the above-mentioned pathogenic fungi of snow blight diseases and of other phytopathies. It has also a durability to low temperatures and can live actively or proliferate with preferable performance of settling on the soil. In order to obtain this filamentous fumgus in a large amount, it may be cultivated in a liquid or solid medium containing ordinary coarbon sourses, nitrogen source, inorganic ions and, if necessary, trace nutrients, as employed in cultivating filamentous fungi.

As the carbon sourse, there may be employed sugars, such as starches and glucose; vegetable wastes, such as coffer grounds, soybean cake, rice bran and wheat bran; alcohols, such as ethanol etc.; organic acids, such as acetic acid etc.;

and oils, such as lard etc. As the nitrogen source, ammonium salts, nitrates, amino acids and so on may be used. As the trace nutrients, small amounts of vitamins, yeast extract and the like may be added to the culture medium.

In the case of liquid culture, a deep culture using an ordinary culture tank may be permitted, wherein the culture is effected under an aerobic condition at a temperature of 2°–34° C., preferably 11°–30° C., at a pH in the range of 3.0–11.5, preferably 4.0–8.0 for 4–10 days to produce a large amount of fungal cells. The resulting culture liquor can be used per se as a microbial product for controlling the snow blight disease, while any appropriate additive may also be incorporated therein.

For collecting the cells of the cultivated fungus, ordinary techniques, such as centrifugation, filtration and so on, may be employed. Here, it is permissible to use a filter aid, such as cerite or parlite, to facilitate filtering of the cells by adding it to the culture medium. The so-separated cells may further be processed by drying by vacuum freeze drying or spray drying or by adding a new carrier thereto.

For the solid culture, there may be exemplified a technique in which a mass of mixture composed of the culture nutrients, such as the carbon sources, nitrogen sourse and inorganic ions as usable also in liquid culture, and a porous light-weighing inorganic carrier substance, such as zeolite, vermiculite or the like, is inoculated with seed cells of the filamentous fungus according to the present invention to effect the cultivation; a technique in which a porous light-weighing inorganic carrier substance, such as mentioned above, is impregnated with the culture nutrients as mentioned above and the resulting mass is innoculated with seed cells of the filamentous fungus according to the present invention to effect the cultivation; or a technique in which a woven plant product, such as straw mat etc., is impregnated with the culture nutrients and the cultivation of the fungus is effected thereon.

The culture of the fungus according to the present invention may also be realized in a closed vessel in a similar manner as in the so-called bottle culture realized for cultivating mushrooms. Here, the culture of the fungus according to the present invention is performed under the same condition as in liquid culture for 7–15 days to proliferate it. After the culture, the culture mixture may preferably be crushed and then, as mentioned above, may be processed by drying the resulting mixture, to adjust the moisture content thereof, in general, at 30% or less, or by admixing to the crushed mixture a dry mass of inorganic filler, such as zeolite or vermiculite, or an organic carrier material, such as rice bran, wheat bran or the like to form a product of appropriate consistency for application.

The microbial product for controlling snow blights according to the present invention may have any appropriate form and may be in the form of, for example, liquid, powder, granules or pellets. It is preferble in some cases that the filamentous fungi according to the present invention are caused to be supported on a fibrous or net-like carrier substance by adsorbing or by cultivating them thereon. For the carrier substance, a biodegradable fibrous or unwoven textile may preferably be employed, such as for example, "Benneto" (trade name, a product of Asahi Chemical Industry Co., Ltd.).

The microbial product for controlling snow blight according to the present invention may be applied to the ground in a dosage of at least 7,500,000 DFU (Colony Forming Unit: Cf. "Shinpen Dojobiseibutsu Jikkenho"—New Eddition of Method of Experiments for Soil-Microorganisms—edited by Soil-Microorganisms Research Association, published from Yokendo, pp 62) of the fungal cells per 1 $m^2$ of the ground by spraying. If a fibrous or net-like biodegradable textile carrier as mentioned above is employed, the dosage should calculate with respect to the fungal cells present on such carrier.

As the carrier, there may be exemplified inorganic substances, such as zeolite, vermiculite and so on, and organic substances, such as rice bran, wheat bran and the like, wherein a particular preference is given for carriers containing, or impregnated with, nutrients effective for the culture of the fungi according to the present invention.

While the content of the living fungal cells in the microbial product for controlling snow blights according to the present invention is not specifically limited so long as it permits to realize application of the above effective dosage, an excessively low content may require a large application amount and may be problematic in particular for applying to the grassy ground of, such as golf course, when the lawn grass becomes hidden under the applied product, so that a pertinent content may be required.

It is preferable, though not always of interest for the case of using a culture liquor as such, that the content of the fungal cells, in particular, in the solid microbial product for controlling snow blight according to the present invention should preferably be at least 150,000 CFU per one gram of the product. It is particularly preferable when the moisture content of the microbial product is not higher than 30%, especially not higher than 15%, since the stability of the microbes in the product will be better and, in particular, an effective content of the microbes can be maintained even on storage in the open field.

The microbial product for controlling snow blights according to the present invention is applied to the ground or to the leaf surface of the objective plant before snow becomes laid on the ground, especially before continuous snow coverage over the ground has occurred. By incorporating a wetting agent, especially sodium carboxymethyl cellulose (e.g. Avicel® of Asahi Chemical Industry Co., Ltd.) in the microbial product according to the present invention in an amount not higher than 30% by weight, preferably not higher than 10% by weight, most preferably within the range of 5–0.5% by weight, for preventing flooding off or washing away of the microbial product, the performance of the microbes for settling on the leaf is increased and the effect for the control of the diseases is promoted. Also the problem of environmental pollution is resolved.

While the amount of application of the microbial product is as described above, the microbial product for controlling snow blghts of, for example, Example 1 given in the following may be applied at a dosage of 10–1,000 grams, preferably 50 grams or more per one square meter. As given in the following Examples, the microbial product for controlling snow blights according to the present invention is effective for all the snow blight diseases, namely, Typhula snow blight (*Typhula incarnata*), Typhula snow blight (*Typhula ishikariensis*), Fusarium snow blight (*Fusarium nivale* f. sp. *graminicola*) Pythium snow blight and Sclerotinia.

THE BEST MODE FOR EMBODYING THE INVENTION

Below, the present invention will be described concretely by way of Reference Example and Examples, wherein it is to be understood that the present invention should not, in any respect, be restricted by such Reference Example and Examples.

REFERENCE EXAMPLES

Sample soils in each golf course in Hokkaido and Fukushima and Fukui prefectures suffered from occurrence of snow blight diseases of the lawn grass were collected. Each one gram of the samples was taken and suspended in 10 ml of sterilized physiological saline (0.7% NaCl) and the resulting suspensions were used as the soil samples for sorting out psychrophiles. A plate of potato dextrose agar medium (PDA) (a product of Eiken Kagaku K.K.) was prepared, on which 0.1 ml of each soil sample was spreader over the plate using a conlage and incubated at 10° C. for a period of 1–2 weeks. Each of the colonies appeard on the PDA plate was placed on a fleshly prepared PDE plate and the plate was incubated at 3° C. for a period of 1–2 weeks. From this, 9 strains of filamentous fungi which had shown colony formation at 10° C. were obtained, among which one strain showed a colony formation at 3° C. The strains of filamentous fungi grown at 1020 C. were identified to be consisting of two of genus Humicola and five of genus Fusarium and two of genus Acremonium. The filamentous fungus that was able to grow at 3° C. was identified as *Humicola grisea* var. *grisea* M6834.

EXAMPLE 1

One spatula amount of *Humicola grisea* var. *grisea* M6834 (deposited under accession No. FERM BP-5452) isolated from the soil of a golf course in Hokkaido was inoculated into a liquid culture medium of pH 6.8 containing 2% of a malt extract (a product of the firm DIFCO), 0.2% of a yeast extract (a product of DIFCO) and 2% of dextrose (a peoduct of Wako Pure Chemical Industries, Ltd.) and was incubated at 26° C. for 6 days under an aerobic condition. The content of the fungal cells of *Humicola grisea* var. *grisea* M6834 in the culture medium was determined to be 3,000,000 CFU per 1 ml of the culture liquor. Using this culture liquor for the seed fungus, a solid culture was carried out. One liter of a culture base containing a mixture of rice bran and rice straw (1/1 in volume ratio) and adjusted to a water content of 60% by weight was charged in a polypropylene bag (Sunbag, tradename of Santomi Sangyo K.K.) to be used for cultivating mushroom and the contents of the bag were then sterilized at 121° C. for 2 hours. After the sterilization, the bag contents were stood to cool and this solid culture medium was inoculated with 20 ml of the above-mentioned seed culture liquor, whereupon the resulting medium was cultivated at 25° C. for two weeks. By this solid culture, a solid culture product having a water content of 45% by weight and a fungal cell content of 450,000 CFU of *Humicola grisea* var. *grisea* M6834 per one gram was obtained. To this solid culture product was admixed dry vermiculate at a mixing ratio of 1/2 (wt./wt.) to prepare a microbial product for controlling snow blight diseases according to the present invention having a cell content of 150,000 CFU and a water content of 15%.

EXAMPLE 2

As the objective fungi to be examined, *Humicola grisea* var. *grisea* M6834 and three other fungi of the genus Humicola, namely, *Humicola alopallonella* IFO7838, *Humicola fuscoatra* IFO9530 and *Humicola grisea* var. *thermoidea* IFO9834 were chosen and were subjected each to a dual culture against the pathogenic fungi of snow blight given below to determine the degree of inhibition of hypha extension (antagonism).

Method for Determining Degree of Inhibition of Hypha Extension

Pathogenic fungi of Typhula snow blights, i.e. *Typhula incarnata* MAFF306126 and MAFF306128, *Typhula ishikariensis* MAFF306132 and MAFF306134; of Fusarium snow blights, i.e. *Fusarium nivale* MAFF101050 and MAFF511030, allocated from the National Institute of Agurobiological Resources of Ministry of Agriculture, Forestry and Fisheries as well as the pathogenic fungi of Pythium snow blight, i.e. *Pythium paddicum* IFO31993 and *Pythium iwayamai* IFO31990, allocated from the juridical foundation Hakko Kenkyusho (research institute of fermentation) were employed. Each of the above fungi was inoculated onto a PDA (supplied from Eiken Kagaku K.K.) and was incubated at 3° C. for a period of 1–2 weeks and the thereby formed colony was employed for the indicator fungus.

A plate prepared by pouring 20 ml of potato dextrose agar (supplied from Eiken Kagaku K.K.) into a glass shell was inoculated with one strain of the fungus to be examined and with another one strain of the indicator fungus at a distance of 50 mm from each other. Each plate with the indicator fungus and the objective fungus was subjected to a dual culture in the dark at 3° C. for 10 days. The amount of extension of the hypha of the indicator fungus in the direction toward the objective fungus was determined. The retardation of hypha extension of the indicator fungus in the dual culture is represented as the activity of the objective fungus for the inhibition of hypha extension. The calculation of the degree of inhibition of hypha extension is achieved by subtracting the hypha extension amount for the indicator fungus upon the dual culture with the objective fungus from the hypha extension amount of the indicator fungus upon the sole culture of only the indicator fungus and dividing the resulting value by the hypha extension amount upon the sole culture of the indicator fungus. Namely, the calculation is based on the following equation:

$$\text{Degree of Inhibition} = \frac{(E_0 - E_1)}{E_0}$$

in which $E_0$ is the hypha extension of the indicator fungi upon the sole culture of only the indicator fungus and $E_1$ is the hypha extension of the indicator fungus upon the dual culture with the objective fungus.

The results are summarized in Tables 1 to 8.

TABLE 1

| Objective Fungi examined | Inhibition[*) |
|---|---|
| *Humicola grisea* var. *grisea* M6834 | 0.93 |
| *Humicola alopallonella* IFO7833 | 0.01 |
| *Humicola fuscoatra* IFO9530 | 0.02 |
| *Humicola grisea* IFO4863 | 0.02 |
| *Humicola grisea* var. *thermoidea* IFO9854 | 0.00 |

Note
[*)Degree of inhibition expressed by degree of hypha extension of the objective fungus toward the indicator fungus *Typhula incarnata* MAFF306126

TABLE 2

| Objective Fungi examined | Inhibition[*) |
|---|---|
| *Humicola grisea* var. *grisea* M6834 | 0.93 |
| *Humicola alopallonella* IFO7833 | 0.02 |
| *Humicola fuscoatra* IFO9530 | 0.02 |

TABLE 2-continued

| Objective Fungi examined | Inhibition*) |
|---|---|
| Humicola grisea IFO4863 | 0.02 |
| Humicola grisea var. thermoidea IFO9854 | 0.00 |

Note
*)Degree of inhibition expressed by degree of hypha extension of the objective fungus toward the indicator fungus *Typhula incarnata* MAFF306128

TABLE 3

| Objective Fungi examined | Inhibition*) |
|---|---|
| Humicola grisea var. grisea M6834 | 0.86 |
| Humicola alopallonella IFO7833 | 0.01 |
| Humicola fuscoatra IFO9530 | 0.00 |
| Humicola grisea IFO4863 | 0.01 |
| Humicola grisea var. thermoidea IFO9854 | 0.01 |

Note
*)Degree of inhibition expressed by degree of hypha extension of the objective fungus toward the indicator fungus *Typhula ishikariensis* MAFF306132

TABLE 4

| Objective Fungi examined | Inhibition*) |
|---|---|
| Humicola grisea var. grisea M6834 | 0.88 |
| Humicola alopallonella IFO7833 | 0.00 |
| Humicola fuscoatra IFO9530 | 0.00 |
| Humicola grisea IFO4863 | 0.02 |
| Humicola grisea var. thermoidea IFO9854 | 0.01 |

Note
*)Degree of inhibition expressed by degree of hypha extension of the objective fungus toward the indicator fungus *Typhula ishikariensis* MAFF306134

TABLE 5

| Objective Fungi examined | Inhibition*) |
|---|---|
| Humicola grisea var. grisea M6834 | 0.95 |
| Humicola alopallonella IFO7833 | 0.03 |
| Humicola fuscoatra IFO9530 | 0.02 |
| Humicola grisea IFO4863 | 0.02 |
| Humicola grisea var. thermoidea IFO9854 | 0.02 |

Note
*)Degree of inhibition expressed by degree of hypha extension of the objective fungus toward the indicator fungus *Fusarium nivale* MAFF101050

TABLE 6

| Objective Fungi examined | Inhibition*) |
|---|---|
| Humicola grisea var. grisea M6834 | 0.95 |
| Humicola alopallonella IFO7833 | 0.02 |
| Humicola fuscoatra IFO9530 | 0.02 |
| Humicola grisea IFO4863 | 0.02 |
| Humicola grisea var. thermoidea IFO9854 | 0.02 |

Note
*)Degree of inhibition expressed by degree of hypha extension of the objective fungus toward the indicator fungus *Fusarium nivale* MAFF511030

TABLE 7

| Objective Fungi examined | Inhibition*) |
|---|---|
| Humicola grisea var. grisea M6834 | 0.95 |
| Humicola alopallonella IFO7833 | 0.02 |
| Humicola fuscoatra IFO9530 | 0.01 |
| Humicola grisea IFO4863 | 0.03 |
| Humicola grisea var. thermoidea IFO9854 | 0.01 |

Note
*)Degree of inhibition expressed by degree of hypha extension of the objecticve fungus toward the indicator fungus *Pythium paddicum* IFO31993

TABLE 8

| Objective Fungi examined | Inhibition*) |
|---|---|
| Humicola grisea var. grisea M6834 | 0.95 |
| Humicola alopallonella IFO7833 | 0.01 |
| Humicola fuscoatra IFO9530 | 0.00 |
| Humicola grisea IFO4863 | 0.00 |
| Humicola grisea var. thermoidea IFO9854 | 0.01 |

Note
*)Degree of inhibition expressed by degree of hypha extension of the objective fungus toward indicator fungus *Pythium iwayamai* IFO31990

As is seen clearly from Tables 1 to 8, *Humicola grisea* var. *grisea* M6834 showed a strong activity of ihhibiting hypha extension to all the pathogenic fungi of *Typhula incarnata* MAFF306126 and MAFF306128, *Typhula ishikariensis* MAFF306132 and MAFF306134, *Fusarium nivale* MAFF101050 and MAFF511030, *Pythium paddicum* IFO30991 and *Pythium iwayamai* IFO31990.

Other filamentous fungi of the genus Humicola examined comparatively had no antagonism to all the indicator fungi and did not proliferate in the experiments at the culture temperature of 3° C. Here, the word "proliferation" means that the rate of extension of hyphae of the examined fungus on extension from the periphery of the colony formed on the agar plate is greater as compared with that of the psychrophilic filamentous fungus pathogenic to Typhula snow blight, namely, *Typhula incarnata*.

EXAMPLE 3

Pathogenic fungi of Typhula snow blights, i.e. *Typhula incarnata* MAFF306126, *Typhula ishikariensis* MAFF306132, and of Fusarium snow blights, i.e. *Fusarium nivale* MAFF101050, allocated from the National Institute of Agurobiological Resources of Ministry of Agriculture, Forestry and Fisheries; as well as the pathogenic fungus of Pythium snow blight, i.e. *Pythium iwayamai* IFO31990, allocated from the juridical foundation Hakko Kenkyusho (research institute of fermentation) were employed. Each of the above fungi was inoculated into 150 ml of a liquid culture medium of pH 6.8 containing 2% of a malt extract (supplied from the firm DIFCO), 0.2% of a yeast extract (supplied from DIFCO) and 2% of dextrose (supplied from Wako Pure Chemical Industries, Ltd.) and the culture was effected in a 500 ml Erlenmeyer flask at 26° C. for 7 days under an aerobic condition.

Each of the resulting culture liquors was used as the source of the pathogenic fungus for infection. Bottles (each having a diameter of 9 cm and a depth of 9 cm) made of polycarbonate each filled with Tenryu sand were sterilized at 121° C. for one hour. After cooling by standing still, seeds of a lawn grass (Penncross) were sown on the surface over the Tenryu sand layer at a seeding density of 20 g per 1 $m^2$ and the seeds were cultivated in an artificial climatic chamber for one week. Onto the so-cultivated growing lawn grass on the sand layer in the polycarbonate bottle, the microbial products for controlling snow blight diseases prepared in Example 1 was sprayed at a dosage of 10, 50, 100 or 200 grams per 1 m². Then, each 2 ml of the above-mentioned culture liquor of the pathogenic fungi were applied to five portions of the lawn growing over the sand layer in each bottle, wherein said five portions were so chosen that the four portions are located around the central portion in a rectangularly spaced relation with each other on the cultivation surface in the bottle.

The test section composed of a number of polycarbonate bottles was subdivided into five plots consisting of (1) experimental plot 1 for examining the disease control performance where the lawn grass was treated by the microbial product for controlling the snow blight and infected with the pathogenic fungi, (2) experimental plot 2 for examining occurrence of damage due to the microbial product itself where the lawn grass was treated only by the microbial product for controlling snow blight, (3) experimental plot 3, a non-treated healthy plot where the lawn grass was grown without any treatment, (4) experimental plot 4, a disease test plot where the lawn grass was infected with each of the pathogenic fungi at the 5 portions mentioned above without treating with the microbial product according to the present invention and (5) comparative plot 5 where the lawn grass was treated with a commercially available conventional controlling agent, i.e. Copper 8-Hydroxyquinoline {Kinondo-80 (trade name, a product of Aguro.Kaneshou K.K.)}, and was infected with the pathogenic fungi. Six polycarbonate bottles with growing lawn grass were used for each experiment in each plot. Five portions in each bottle were infected with the pathogenic fungus and, hence, 5×6= 30 portions were examined for the occurrence of disease in each test. The lawn grass was maintained in the dark at 3° C. for testing occurence of snow blight. Over the lawn grass, a glass shell filled with 20 ml of sand was placed as a weight for simulating the condition of laid snow in the field pressing onto the grass. After 3 weeks, bottles were taken out of the artificial climatic chamber and the lawn grass was examined for the occurrence of snow blight at each infected portion to determine the number of morbid portions among the 30 infected portions (moridity). The results are summarized in Tables 9 to 12.

TABLE 9

| Experimental plot | Dosage of microbial product | Infection with T. incarnata MAFF306126 | Morbidity (among 30) |
| --- | --- | --- | --- |
| Plot 1 (Control test) | 10 g/m² | 5 × 2 ml/Bottle | 4 |
| | 50 g/m² | 5 × 2 ml/Bottle | 3 |
| | 100 g/m² | 5 × 2 ml/Bottle | 3 |
| | 200 g/m² | 5 × 2 ml/Bottle | 3 |
| Plot 2 (Damage test) | 10 g/m² | | 0 (Healthy) |
| | 50 g/m² | | 0 (Healthy) |
| | 100 g/m² | | 0 (Healthy) |
| | 200 g/m² | | 0 (Healthy) |
| Plot 3 (Healthy) | | | 0 (Healthy) |
| Plot 4 (Disease test) | | 5 × 2 ml/Bottle | 28 |
| Plot 5 (Compar. test) | | 5 × 2 ml/Bottle | 4 |

TABLE 10

| Experimental plot | Dosage of microbial product | Infection with T. incarnata MAFF306132 | Morbidity (among 30) |
| --- | --- | --- | --- |
| Plot 1 (Control test) | 10 g/m² | 5 × 2 ml/Bottle | 3 |
| | 50 g/m² | 5 × 2 ml/Bottle | 3 |
| | 100 g/m² | 5 × 2 ml/Bottle | 2 |
| | 200 g/m² | 5 × 2 ml/Bottle | 2 |
| Plot 2 (Damage test) | 10 g/m² | | 0 (Healthy) |
| | 50 g/m² | | 0 (Healthy) |
| | 100 g/m² | | 0 (Healthy) |
| | 200 g/m² | | 0 (Healthy) |
| Plot 3 (Healthy) | | | 0 (Healthy) |
| Plot 4 (Disease test) | | 5 × 2 ml/Bottle | 30 |
| Plot 5 (Compar. test) | | 5 × 2 ml/Bottle | 3 |

TABLE 11

| Experimental plot | Dosage of microbial product | Infection with F. nivale MAFF101050 | Morbidity (among 30) |
| --- | --- | --- | --- |
| Plot 1 (Control test) | 10 g/m² | 5 × 2 ml/Bottle | 4 |
| | 50 g/m² | 5 × 2 ml/Bottle | 4 |
| | 100 g/m² | 5 × 2 ml/Bottle | 2 |
| | 200 g/m² | 5 × 2 ml/Bottle | 2 |
| Plot 2 (Damage test) | 10 g/m² | | 0 (Healthy) |
| | 50 g/m² | | 0 (Healthy) |
| | 100 g/m² | | 0 (Healthy) |
| | 200 g/m² | | 0 (Healthy) |
| Plot 3 (Healthy) | | | 0 (Healthy) |
| Plot 4 (Disease test) | | 5 × 2 ml/Bottle | 30 |
| Plot 5 (Compar. test) | | 5 × 2 ml/Bottle | 3 |

TABLE 12

| Experimental plot | Dosage of microbial product | Infection with P. iwayamai IFO31990 | Morbidity (among 30) |
| --- | --- | --- | --- |
| Plot 1 (Control test) | 10 g/m² | 5 × 2 ml/Bottle | 2 |
| | 50 g/m² | 5 × 2 ml/Bottle | 2 |
| | 100 g/m² | 5 × 2 ml/Bottle | 2 |
| | 200 g/m² | 5 × 2 ml/Bottle | 2 |
| Plot 2 (Damage test) | 10 g/m² | | 0 (Healthy) |
| | 50 g/m² | | 0 (Healthy) |
| | 100 g/m² | | 0 (Healthy) |
| | 200 g/m² | | 0 (Healthy) |
| Plot 3 (Healthy) | | | 0 (Healthy) |
| Plot 4 (Disease test) | | 5 × 2 ml/Bottle | 29 |
| Plot 5 (Compar. test) | | 5 × 2 ml/Bottle | 2 |

As is clear from the above Tables 9 to 12, the microbial product for controlling snow blight according to the present invention showed an inhibitive effect to snow blight diseases, at a dosage of 10 g/m² (corresponding to 1,500,000 CFU) or greater, comparable to the conventional controlling agent Copper 8-Hydroxyquinoline {Kinondo-80 (trade name, a product of Aguro.Kaneshou K.K.)}. It was also confirmed that the microbial product for controlling snow blight diseases according to the present invention has no influence on Penncross.

EXAMPLE 4

A field test for controlling snow blight diseases was carried out in a golf course in Atsuta District in Hokkaido on a putting green of Penncross damaged in the foregoing year by snow blight diseases by *Typhula incarnata, Typhula ishikariensis, Fsarium nivale* and *Pythium iwayamai*. The microbial product of Example 1 (*Humicola grisea* var. *grisea* M6284) was sprayed onto the test plots on the patting green before snowfall in the middle of November. Two plots of each 1 m² were alloted to the test of the above microbial product. Dosages of 10, 50, 100, 200 and 500 g/m² were employed. As the reference tests, a non-treatment plot for testing without treatment and a cupper-treatment plot for testing with a commercial agricultural organic copper chemical (Copper 8-Hydroxyquinoline {Kinondo-80 (trade name, a product of Aguro Kaneshou K.K.)}), applied in 500-fold dilution at a dosage of 1 liter per m², were settled. In April in the next year, upon the thawing of the laid snow, each test plot was visually inspected and photographed. Based on the photograph, an image analysis was incorporated wherein the green colored healthy portion of the lawn grass is converted into black and the disease-damaged portion thereof is converted into white, wherefrom the surface areas of the portions damaged by the snow blight are estimated optically. The proportion of occurrence of snow blight, namely the morbidity rate is represented by the surface area of the damaged portion per m² in %. The results are summarized in Table 13.

TABLE 13

| | Morbidity Rate (%) | | |
|---|---|---|---|
| Experimental Plots | 1st Test | 2nd Test | Average |
| Non-treatment plot | 88 | 79 | 83.5 |
| Copper-treatment plot | 5 | 4 | 4.5 |
| Test plots*) | | | |
| 10 g/m² | 14 | 12 | 13.0 |
| 50 g/m² | 7 | 5 | 6.0 |
| 100 g/m² | 5 | 4 | 4.5 |
| 200 g/m² | 3 | 2 | 2.5 |
| 500 g/m² | 3 | 1 | 2.0 |

Note
*)Treatment with *Humicola grisea var. grisea* M6284

As is clear from Table 13, the morbidity rate was low in the test plots with dosages of the microbial product according to the present invention of Example 1 in the range from 50 t 500 g/m² which is comparable to, or even superior than, that obtained by the commercial organic copper chemical. However, in the test plot with a dosage of 10 g/m², snow blight disease was found, though slightly, wherefrom it is seen that an effective dosage in the open field may be at least 50 g/m² (corresponding to 7,500,00 cfu) for this microbial product.

A sample soil was taken from each experimental plot at the interfacial portion between the lawn grass and the soil and was examined for the existence of the filamentous fungus *Humicola grisea* var. *grisea* M6384 by a culture on a plate, prepared by charging a glass shell with 20 ml of potato dextrose agar (supplied from Eiken Kagaku K.K.), effected at 3° C. for 14 days, whereby it was found that the filamentous fungus according to the present invention, i.e. *Humicola grisea* var. *grisea* M6834, was detected at a content of 5,000–20,000 CFU per 1 g of the soil in the test plots sprayed with the microbial product of Example 1, showing a settling ability of the above filamentous fungus according to the present invention on soils in the open field.

EXAMPLE 5

*Humicola grisea* var. *grisea* M6834 was inoculated into a liquid culture medium of pH 6.8 containing 2% of a malt extract (supplied from the firm DIFCO), 0.2% of a yeast extract (supplied from DIFCO) and 2% of dextrose (supplied from Wako Pure Chemical Industries, Ltd.) and the culture was effected at 26° C. for 6 days under an aerobic condition. The population of living cells of *Humicola grisea* var. *grisea* M6834 were found to be 3,000,000 CFU per 1 ml of the culture liquor. This culture liquor was filtered to separate snd collect only the fungal cells. The so-separated fungal cells were placed in an agate mortar and thereto was added an amount of a distilled water for injection to suspend the cells so as to prepare a 20% sample solution. On the other hand, 10 male mice of SPF, ICR strain (supplied from Nippon SLC K.K.) of 4 weeks age were preliminarily breeded for one week. To each of these five weeks aged mice were adminstered orally the above 20% sample solution in a dosage of 0.5 ml per 10 g body weight. To another 10 mice in a non-treatment group were adminitered only physiological saline. All the mice in the group administerd by the sample solution showed no abnormal behavior, such as piloerection, diarrhea, abnormal motion etc., from the time directly after the oral administration. Also in the observation during the period till the last day of the second week of breeding, no difference in the appearance was recognized between the group treated by the oral administration of the sample solution and the group without treatment. The body weight of each mouse was observed at the first, third, 8th and 14th day of the administration. Here, also no difference was recognized between the group treated by the sample solution and the group without treatment. There was no animal which was dead during the examination period. The 50% lethal dose (LD50) of *Humicola grisea* var. *grisea* M6834 for mouse was found to be 10,000 mg/kg or higher.

EXAMPLE 6

*Humicola grisea* var. *grisea* M6834 was inoculated into a liquid culture medium of pH 6.8 containing 2% of a malt extract (supplied from the firm DIFCO), 0.2% of a yeast extract (supplied from DIFCO) and 2% of dextrose (supplied from Wako Pure Chemical Industries, Ltd.) and the culture was effected at 26° C. for 6 days under an aerobic condition. The population of living cells of *Humicola grisea* var. *grisea* M6834 was found to be 3,000,000 CFU per 1 ml of the culture liquor. Using this culture liquor, a growth inhibition test was performed for each seedling of rice, corn, potato, pea, barley and wheat. The test was carried out in a water culture system using a 500-fold diluted hydroponic solution of "Hyponex (5.10.5)" (trade name; Murakami Bussan K.K.) using "Rhyzometer" (trade name; Uchidayoko K.K.). The culture section was subdivided into a non-treatment test plot in which each seedling of the abovementioned crops was cultivated using a cultivation solution consisting of only an equivolume mixture of the hydroponic solution and distilled water and an inhibition test plot in which each seedling was cultivated in the "Rhyzometer" using a growth inhibitive cultivation solution consisting of an equivolume mixture of the hydroponic solution and the above-mentioned culture liquor. The water cultivation was effected for 6 days in such a manner that the seedling was soaked in the cultivation solution. By this test, it was observed that the growth inhibitive cultivation solution allowed a growth of the seedling of each of the above-mentioned plants which was by about 1–3% retarded as compared with that in the non-treatment plot, while no morbid symptom of yellowing, withering or blighting was recognized. No residue of *Humicola grisea* var. *grisea* M6834 was detected from cut section of the plants, so that it was recognizable that *Humicola grisea* var. *grisea* M6834 does not exhibit any pathogenicity to the crops of rice, corn, potato, pea, barley and wheat.

EXAMPLE 7

The solid culture product prepared in Example 1 which is a microbial product for controlling snow blight diseases according to the present invention was mixed with a dry mass of vermiculite in a mixing ratio (wt./wt.) of 3:1 (moisture content 38%), 2:1 (moisture content 30%), 1:1 (moisture content 23%), 1:2 (moisture content 15%) or 1:3 (moisture content 11%), whereupon the mixture was subjected to a storage test at 25° C. for 60 days. The results are summarized in Table 14.

TABLE 14

| Mix. proportion (wt./wt.) | | Water cont. (wt. %) | Cell population of M6834 ($\times 10^4$ CFU/g) | | |
|---|---|---|---|---|---|
| Culture product M6834 | Dry vermiculite | | direct after Mixing | after 30 days | after 60 days |
| 1 | — | 45 | 45 | 25 | 18 |
| 3 | 1 | 38 | 34 | 21 | 16 |
| 2 | 1 | 30 | 30 | 28 | 27 |
| 1 | 1 | 23 | 23 | 24 | 23 |
| 1 | 2 | 15 | 15 | 16 | 17 |
| 1 | 3 | 11 | 11 | 11 | 10 |

As seen from Table 14, no decrease in the number of living fungal cells of *Humicola grisea* var. *grisea* M6834 occurs so long as the water content of the microbial product is 30% by weight or lower. Therefore, it is necessary in storing the microbial product of the filamentous fungus *Humicola grisea* var. *grisea* M6834 according to the present invention to maintain a condition of a water content of 30% or lower, preferably 15% or lower.

EXAMPLE 8

In order to evaluate the inhibitive performance (antagonistic activity) of *Humicola grisea* var. *grisea* M6834 to pathogenic fungi, the pathogenic fungi as given below were collected and the antagonism of *Humicola grisea* var. *grisea* M6834 to each of these pathogenic fungi was estimated.

Method for Estimating the Antagonism

Each of 49 strains of the pathognic fungi for sbow blight diseases, namely, *Pythium paddicum* IFO31993, IFO31994 and IFO31995; *Pythium graminicola* IFO31996, IFO31997, IFO31998 and IFO32330; *Pythium iwayamai* IFO31990, IFO31991 and IFO31992; and *Myriosclerotinia borealis* IFO30319, allocated from the juridical foundation Hakko Kenkyusho; *Typhula incarnata* MAFF306126, MAFF306127, MAFF306128, MAFF306129 and MAFF306130; *Typhula ishikariensis* MAFF306132, MAFF306133, MAFF306134, MAFF306135, MAFF306136, MAFF306138, MAFF306139, MAFF306140, MAFF306141, MAFF306142, MAFF306143, MAFF306144, MAFF306145, MAFF306146, MAFF306148 and MAFF306149; *Fusarium nivale* MAFF101047, MAFF101048, MAFF101049, MAFF101050, MAFF235733, MAFF235741, MAFF235948, MAFF236681, MAFF236682, MAFF236683, MAFF305694, MAFF510557, MAFF511110, MAFF305032 and MAFF305033, allocated from the National Institute of Agurobiological Resources of Ministry of Agriculture, Forestry and Fisheries, was inoculated onto a potato dextrose agar medium (PDA) (supplied from the firm Eiken Kagaku K.K.) and incubated at 3° C. for a period of 1–3 weeks and the resulting colonies on the PDA medium were used as the sources of the pathogenic fungi for estimating the antagonism.

One liter of PDA medium was heat sterilized and then cause to cool by standing under an ambient temperature. When the temperature of the medium had decsended down to 60° C., 100 ml of a culture liquor, which was obtained by a separately conducted culture of *Humicola grisea* var. *grisea* M6834 in a liquid culture medium of pH 6.8 containing 2% of a malt extract (supplied from the firm DIFCO), 0.2% of a yeast extract (supplied from DIFCO) and 2% of dextrose (supplied from Wako Pure Chemical Ind., Ltd.) at 26° C. for 7 days under an aerobic condition, were admixed thereto. The resulting 1.1 liters of the mixed liquor were poured into a plate culture vessel for bioassay having a length of 400 mm, a width of 210 mm and a depth of 27 mm (supplied from Kaise Rika K.K.) and were cooled to solidity (the resulting solidified medium is denoted hereinafter as "the solid mixed medium"). Separately herewith, a solidified PDA medium was prepared as a reference medium by cooling 1.0 liter of liquid PDA in a plate culture vessel for bioassay. Each of the colonies of the afore-mentioned pathogenic fungi for use for the antagonism estimation formed on the PDA medium was isolated therefrom by stamping out using a cork borer having a diameter of 6 mm to prepare a disc of PDA of each pathogenic fungus of snow blight. Each of the so-isolated discs was placed on the solid mixed medium mentioned above, on the one hand, and on the above-mentioned reference medium, on the other hand.

The plate culture vessel with the solid mixed medium on which the PDA disc of each pathogenic fungus was placed and the plate culture vessel with the reference medium on which the PDA disc of each pathogenic fungus was also placed were cultivated in the dark at 3° C. for 8 days. The antagonistic activity to pathogenic fungus was determined from the amount of extension of the hyphae from the colony of each fungus pathogenic to snow blight on the PDA disc towards the reference medium on which the disc was placed, on the one hand, and the amount of extension of the hyphae from the colony of each fungus pathogenic to snow blight on the PDA disc towards the solid mixed medium on which the disc was placed, on the other hand, by the following calculation equation:

$$\text{Antagonistic activity } (\%) = \frac{D_0 - D_1}{D_0} \times 100$$

in which $D_0$ is the diameter of the outer extension limit of the hyphae around the colony placed on the reference medium and $D_1$ is the diameter of the outer extension limit of the hyphae around the colony placed on the solid mixed medium.

It should be understood that the greater this value, the higher will be the antagonistic activity of the fungus *Humi-* cola grisea var. grisea M6834 against the pathogenic fungus examined. If this value amounts to 100(%), the antagonistic activity is quite high and is represented by the mark "++". If this value is 50(%) or greater, this indicates a moderate antagonistic activity and is represented by the mark "+", if this value is 10(%) or greater, this means an existence of antagonistic activity and is represented by the mark "±" and if this value is not higher than 10(%), this means a scarce or even lacking antagonism and is represented by "0". The test results are summarized in Table 15. The filamentous fungus Humicola grisea var. grisea M6834 showed a high antagonistic activity to all the examined pathogenic fungi of snow blight.

TABLE 15

| Test No. | IFO No. | Fungus strain | Host plant | Ant.*) |
|---|---|---|---|---|
| 1 | 31993 | Pythium paddicum | Barley | ++ |
| 2 | 31994 | Pythium paddicum | Wheat | ++ |
| 3 | 31995 | Pythium paddicum | Wheat | ++ |
| 4 | 31996 | Pythium graminicola | Barley | ++ |
| 5 | 31997 | Pythium graminicola | Barley | ++ |
| 6 | 31998 | Pythium graminicola | Barley | ++ |
| 7 | 32330 | Pythium graminicola | Zoysia matrella | ++ |
| 8 | 30319 | Myriosclerotinia borealis | Orchard grass | + |
| 9 | 31990 | Pythium iwayamai | Wheat | ++ |
| 10 | 31991 | Pythium iwayamai | Wheat | ++ |
| 11 | 31992 MAFF No. | Pythium iwayamai | Barley | ++ |
| 12 | 101047 | Fusarium nivale (Fries) Cesati | Wheat | ++ |
| 13 | 101049 | Fusarium nivale (Fries) Cesati | Wheat | ++ |
| 14 | 101050 | Fusarium nivale (Fries) Cesati | Barley | ++ |
| 15 | 235733 | Fusarium nivale (Fries) Cesati | Bent grass | ++ |
| 16 | 235741 | Fusarium nivale (Fries) Cesati | Bent grass | ++ |
| 17 | 235948 | Fusarium nivale (Fries) Cesati | Bent grass | ++ |
| 18 | 236681 | Fusarium nivale (Fries) Cesati | Barley | ++ |
| 19 | 236682 | Fusarium nivale (Fries) Cesati | Barley | ++ |
| 20 | 236683 | Fusarium nivale (Fries) Cesati | Barley | ++ |
| 21 | 305694 | Fusarium nivale (Fries) Cesati | Reed canary grass | ++ |
| 22 | 510557 | Fusarium nivale (Fries) Cesati | Rescue grass | ++ |
| 23 | 511110 | Fusarium nivale (Fries) Cesati | Rice | ++ |
| 24 | 511030 | Fusarium nivale (Fries) Cesati | Italian ryegrass | ++ |
| 25 | 305031 | Micronectriella nivalis Booth | Wheat | ++ |
| 26 | 305032 | Micronectriella nivalis Booth | Italian ryegrass | ++ |
| 27 | 305033 | Micronectriella nivalis Booth | Rye | ++ |
| 28 | 306126 | Typhula incarnata Lasch ex Pries | Alfalfa | ++ |
| 29 | 306127 | Typhula incarnata Lasch ex Pries | Meadow fescue | ++ |
| 30 | 306128 | Typhula incarnata Lasch ex Pries | Japanese white birch | ++ |
| 31 | 306129 | Typhula incarnata Lasch ex Pries | Rice | ++ |
| 32 | 306130 | Typhula incarnata Lasch ex Pries | Orchard grass | ++ |
| 33 | 306132 | Typhula ishikariensis Imai | Perennial ryegrass | + |

TABLE 15-continued

| Test No. | IFO No. | Fungus strain | Host plant | Ant.*) |
|---|---|---|---|---|
| 34 | 306133 | Typhula ishikariensis Imai | Wheat | + |
| 35 | 306134 | Typhula ishikariensis Imai | Wheat | + |
| 36 | 306135 | Typhula ishikariensis Imai | Orchard grass | + |
| 37 | 306136 | Typhula ishikariensis Imai | Alfalfa | + |
| 38 | 306138 | Typhula ishikariensis Imai | Kayatsurigusa | + |
| 39 | 306139 | Typhula ishikariensis Imai | Orchard grass | + |
| 40 | 306140 | Typhula ishikariensis Imai | Orchard grass | + |
| 41 | 306141 | Typhula ishikariensis Imai | Wheat | + |
| 42 | 306142 | Typhula ishikariensis Imai | Kentucky blue grass | + |
| 43 | 306143 | Typhula ishikariensis Imai | Grasses | + |
| 44 | 306144 | Typhula ishikariensis Imai | Orchard grass | + |
| 45 | 306145 | Typhula ishikariensis Imai | Rushes | + |
| 46 | 306146 | Typhula ishikariensis Imai | Barley | + |
| 47 | 306147 | Typhula ishikariensis Imai | Orchard grass | + |
| 48 | 306148 | Typhula ishikariensis Imai | Wheat | + |
| 49 | 306149 | Typhula ishikariensis Imai | Grasses | + |

Note
*)Antagonistic activity estimated

EXAMPLE 9

150 ml of a liquid culture medium of pH 8.6 containing 2% of a malt extract (supplied from the firm DIFCO), 0.2% of a yeast extract (supplied from the firm DIFCO) and 2% of dextrose (supplied from Wako Pure Chemical Ind., Ltd.) were inoculated with a pathogenic fungus of Typhula snow blight, i.e. Typhula incarnata MAFF305031 alocated from the National Institute of Agurobiological Resources of Ministry of Agriculture, Forestry and Fisheries and were incubated in a 500 ml Erlenmeyer flask at 6° C. for 7 days under an aerobic condition. The resulting culture liquor was used as the source of pathogenic fungus of snow blight of wheat for infecting the plant terewith. Thus, a polycarbonate bottle (9 cm diameter, 9 cm depth) filled with Tenryu sand was sterilized at 121° C. for 1 hour. After cooling by standing still, 5 seeds of wheat (Norin No. 1) were placed on the surface of the sand layer in the bottle and were cultivated in a climatic chamber for 3 weeks. Onto the leafs of the growing wheat, a mixture of the microbial product prepared in Example 1 with 3% of Avicel® RC591 (trade name, a product of Asahi Chemical Ind. Co., Ltd.) was sprayed at a dosage per 5 stocks per bottle of 0.06 g (10 g/m$^2$), 0.32 g (50 g/m$^2$), 0.63 g (100 g/m$^2$) or 1.26 g (200 g/m$^2$). The infection of the plant with the pathogenic fungus was effected using each 2 ml of the above-mentioned culture liquor to be applied onto the leafs of the five stocks of the plant in the bottle.

The test was carried out in four experimental plots of plant growing bottles, in which plot 1 (test plot) was alloted for examining the contolling effect by subjecting the plant to the spray application of the microbial product and then to the infection with the patogenic fungus, plot 2 (blank test plot)

was alloted for examining occurrence of any damage caused by the microbial product itself by subjecting the plant only to the application of the microbial product, plot 3 (healthy plot) was alloted for examining a healthy growth of the plant without incorporating any treatment by application of the microbial fungus nor infection with the pathogenic fungus and plot 4 (morbid plot) was alloted for the examination of free morbid effect of infection with the pathogenic fungus on the plant without incorporating application of the microbial product according to the present invention. In each test, 6 bottles with 5 stocks of wheat seedling, thus, 30 stocks (5×6) of wheat seedling were used. For testing occurrence of snow blight, the bottles were maintained in the dark at 3° C. in a climatic chamber. After 3 weeks, the bottled were taken out of the climatic chamber and were inspected for the morbidity, i.e. the proportion of the number of morbid stocks to the total of 30 tested stocks. The results are summarized in Table 16.

TABLE 16

| Experimental plot | Dosage of microbial product | Infection with fungus MAFF305031 | Morbidity (stocks/30 stocks) |
|---|---|---|---|
| 1: Test plot | 10 g/m$^2$ | 5 × 2 ml/bottle | 1 |
|  | 50 g/m$^2$ |  | 1 |
|  | 100 g/m$^2$ |  | 0 |
|  | 200 g/m$^2$ |  | 0 |
| 2: Blanc test plot | 10 g/m$^2$ | 5 × 2 ml/bottle | 0 (Healthy) |
|  | 50 g/m$^2$ |  | 0 (Healthy) |
|  | 100 g/m$^2$ |  | 0 (Healthy) |
|  | 200 g/m$^2$ |  | 0 (Healthy) |
| 3: Healthy plot |  |  | 0 (Healthy) |
| 4: Morbid plot |  | 5 × 2 ml/bottle | 28 |

EXAMPLE 10

*Humicola grisea* var. *grisea* M6834 was inoculated into a liquid culture medium of pH 6.8 containing 2% of a malt extract (supplied from the firm DIFCO), 0.2% of a yeast extract (supplied from the firm DIFCO) and 2% of dextrose (supplied from Wako Pure Chemical Industries, Ltd.) and the culture was effected at 26° C. for 6 days under an aerobic condition. The population of the living cells of *Humicola grisea* var. *grisea* M6834 was found to be 3,000,000 CFU per 1 ml of the culture liquor. Using this culture liquor, a growth inhibition test was performed for seedling of rapeseed. The test was carried out in a water culture system using a 500-fold diluted hydroponic solution of "Hyponex (5.10.5)" (trade name; a product of Murakami Bussan K.K.) using "Rhyzometer" (trade name; Uchidayoko K.K.). The culture section was subdivided into a non-treatment test plot in which each seedling of the above-mentioned crops was cultivated using a cultivation solution consisting of only an equivolume mixture of the hydroponic solution and distilled water and an inhibition test plot in which each seedling was cultivated in the "Rhyzometer" using a growth inhibitive cultivation solution consisting of an equivolume mixture of the hydroponic solution and the above-mentioned culture liquor. The water cultivation was effected for 6 days in such a manner that the radicles were soaked in the cultivation solution. By this test, it was observed that the groth inhibitive cultivation solution allowed a growth of the seedling of rapeseed which was by about 2% retarded as compared with that in the non-treatment plot, while no morbid symptom of yellowing, withering or blighting was recognized. No residue of *Humicola grisea* var. *grisea* M6834 was detected from cut section of the stem of rapeseed, so that it was recognizable that *Humicola grisea* var. *grisea* M6834 does not exhibit any pathogenicity to rapeseed.

EXAMPLE 11

The inhibitive performance (antagonistic activity) of *Humicola grisea* var. *grisea* M6834 against the following phytopathogenic fungi were estimated.

Method for Estimating the Antagonism

Each of the phytopathognic fungi given in Tables 17 and 18, allocated from the juridical foundation Hakko Kenkyusho and from the National Institute of Agurobiological Resources of Ministry of Agriculture, Forestry and Fishery, was inoculated onto a potato dextrose agar medium (PDA) (supplied from the firm Eiken Kagaku K.K.) and cultivated at 26° C. for a period of 5–8 days and the resulting colonies on the PDA medium were used as the sources of the pathogenic fungi for estimating the antagonism.

One liter of PDA medium was heat sterilized and then cooled by standing under an ambient temperature. When the temperature of the medium had descended down to 60° C., 100 ml of a culture liquid, which was obtained by a separately conducted culture of *Humicola grisea* var. *grisea* M6834 in a liquid culture medium of pH 6.8 containing 2% of a malt extract (supplied from the firm DIFCO), 0.2% of a yeast extract (supplied from the firm DIFCO) and 2% of dextrose (supplied from Wako Pure Chemical Ind., Ltd.) at 26° C. for 7 days under an aerobic condition, were admixed thereto. The resulting 1.1 liters of the mixed liquor were poured into a plate culture vessel for bioassay having a length of 400 mm, a width of 210 mm and a depth of 27 mm (supplied from Kaise Rika K.K.) and were cooled to solidify (the resulting solidified medium is denoted hereinafter as "the solid mixed medium").

Separately herewith, a solidified PDA medium was prepared as a reference medium by cooling 1.0 liter of liquid PDA in a plate culture vessel for bioassay. Each of the colonies of the afore-mentioned pathogenic fungi for estimating the antagonism formed on the PDA medium was isolated therefrom by stamping out using a cork borer having a diameter of 6 mm to prepare a disc of PDA medium of each phytopathogenic fungus. Each of the so-isolated discs was placed on the above-mentioned solid mixed medium, on the one hand, and on the above-mentioned reference medium, on the other hand.

The plate culture vessel with the solid mixed medium on which the PDA disc of each pathogenic fungus was placed and the plate culture vessel with the reference medium on which the PDA disc of each pathogenic fungus was also placed were cultivated in the dark at 26° C. for 5 days. The antagonistic activity to pathogenic fungus was determined from the amount of extension of the hyphae from the colony of each phytopathogenic fungus on the PDA disc towards the reference medium on which the disc was placed, on the one hand, and the amount of extension of the hyphae from the colony of each phytopathogenic fungus on the PDA disc towards the solid mixed medium on which the disc was placed, on the other hand, by the following calculation equation:

$$\text{Antagonistic activity (\%)} = \frac{D_0 - D_1}{D_0} \times 100$$

in which $D_0$ is the diameter of the outer extension limit of the hyphae around the colony placed on the reference medium and $D_1$ is the diameter of the outer extension limit of the hyphae around the colony placed on the solid mixed medium.

It should be understood that the greater this value, the higher will be the antagonistic activity of the fungus *Humicola grisea* var. *grisea* M6834 aganst the pathogenic fungus examined. If this value amounts to 100(%), the antagonistic activity is quite high and is represented by the mark "++". If this value is 50(%) or greater, this indicates a moderate antagonistic activity and is represented by the mark "+", if this value is 10(%) or greater, this means an existence of antagonistic activity and is represented by the mark "+" and if this value is not higher than 10(%), this means a scarce or even lacking antagonism and is represented by "0". The test results are summarized in Tables 17 and 18. The filamentous fungus *Humicola grisea* var. *grisea* M6834 showed a high antagonistic activity to all the examined phytopathogenic fungi.

TABLE 17

| Pathogenic fungi | IFO number | Antag. activity |
| --- | --- | --- |
| *Pythium ultimim* | 32210 | ++ |
| *Pythium torulosum* | 32166 | ++ |
| *Pythium vanterpoolii* | 31924 | ++ |
| *Pythium aphanidermatum* | 7030 | ++ |

TABLE 18

| Pathogenic fungi | MAFF number | Antag. act. |
| --- | --- | --- |
| *Rhizoctonia solani* | 305223 | + |
| *Rhizoctonia solani* | 305246 | + |
| *Rhizoctonia solani* | 305241 | + |
| *Rhizoctonia solani* | 305231 | + |
| *Rhizoctonia sp.* (binucleate) | 305294 | + |
| *Pythium myriotylum* | 305636 | ++ |
| *Carvularia genicuata* | 305365 | ++ |
| *Carvularia geniculata* | 510202 | ++ |
| *Carvularia lunata* | 510746 | + |
| *Carvularia trifolii* | 305097 | + |
| *Bipolaris sorokiniana* | 511217 | + |
| *Bipolaris sorokiniana* | 511334 | + |
| *Fusarium avenaceam* | 101040 | + |
| *Fusarium graminearum* | 101033 | + |
| *Sclerotinia homoeocarpa* Bennet | 235854 | + |
| *Sclerotinia homoeocarpa* Bennet | 235855 | + |
| *Sclerotinia homoeocarpa* Bennet | 235856 | + |
| *Sclerotinia homoeocarpa* Bennet | 235857 | + |
| *Sclerotinia homoeocarpa* Bennet | 235858 | + |
| *Sclerotinia homoeocarpa* Bennet | 235859 | + |
| *Pythium graminicola* Subramaniam | 235183 | + |
| *Pythium graminicola* Subramaniam | 235836 | + |
| *Pythium graminicola* Subramaniam | 305577 | + |
| *Carvularia geniculata* (Tracy et earle) Beodini | 235525 | + |
| *Carvularia geniculata* (Tracy et earle) Beodini | 235745 | + |
| *Carvularia geniculata* (Tracy et earle) Beodini | 235862 | + |
| *Carvularia geniculata* (Tracy et earle) Beodini | 235863 | + |
| *Gaeumannomyces graminis* (Saccardo) V. Arx et Olivier | 305163 | ++ |
| *Gaeumannomyces graminis* (Saccardo) V. Arx et Olivier | 305164 | ++ |
| *Gaeumannomyces graminis* (Saccardo) V. Arx et Olivier | 305165 | ++ |
| *Gaeumannomyces graminis* (Saccardo) V. Arx et Olivier | 305166 | ++ |
| *Gaeumannomyces graminis* (Saccardo) V. Arx et Olivier | 305168 | ++ |
| *Gaeumannomyces graminis* (Saccardo) V. Arx et Olivier | 305169 | ++ |
| *Gaeumannomyces graminis* (Saccardo) V. Arx et Olivier | 305170 | ++ |
| *Gaeumannomyces graminis* (Saccardo) V. Arx et Olivier | 305171 | ++ |

EXAMPLE 12

Pathogenic fungi of Typhula snow blights, i.e. *Typhula incarnata* MAFF306126, *Typhula ishikariensis* MAFF306132, and of Fusarium snow blights, i.e. *Fusarium nivale* MAFF101050, allocated from the National Institute of Agurobiological Resources of Ministry of Agriculture, Forestry and Fisheries; as well as the pathogenic fungus of Pythium snow blight, i.e. *Pythium iwayamai* IFO31990, allocated from the juridical foundation Hakko Kenkyusho were employed. Each of the above fungi was inoculated into 150 ml of a liquid culture medium of pH 6.8 containing 2% of a malt extract (supplied from the firm DIFCO), 0.2% of a yeast extract (supplied from the firm DIFCO) and 2% of dextrose (supplied from Wako Pure Chemical Industries, Ltd.) and the culture was effected in a 500 ml Erlenmeyer flask at 26° C. for 7 days under an aerobic condition.

Each of the resulting culture liquors was used as the source of the pathogenic fungus for infection. A number of polycarbonate bottles (each having a diameter of 9 cm diameter and a depth of 9 cm) each filled with Tenryu sand were sterilized at 121° C. for one hour. After cooling by standing still, seeds of a lawn grass (Penncross) were sown over the surface of the Tenryu sand layer in each bottle at a seeding density of 20 g per 1 $m^2$ and the seeds were cultivated in an artificial climatic chamber for one week.

The experimental section composed of these bottles was subdivided into four plots consisting of two testing plots 1 and 2 for examining the disease control performance of the microbial product of Example 1 on infection with the pathogenic fungi and additional two testing plots 3 and 4 for examining the disease control performance of the microbial product of Example 1 with two commercially available wetting agentres pectively on infection with the pathogenic fungi.

In plot 1, the microbial product prepared in Example 1 was applied to the so-cultivated growing lawn grass on the sand layer in each of the polycarbonate bottles. In plot 2, a wetting agent-containing microbial product prepared by blending the microbial product of Example 1 with 0.3, 0.5, 1.0, 3.0, 5.0 or 10% by weight of sodium-carboxymethyl cellulose (Na-CMC) (e.g. Avicel® trade name) was applied to the growing lawn grass on the sand layer in each of the polycarbonate bottles at a dosage of the microbial product of 10 g/$m^2$ or 50 g/$m^2$. Then, the lawn grass growing in each of the bottles in plots 1 and 2 was infected at each of five portions on the lawn grass-planted face of the sand layer, chosen in such a manner that four portions are located in a rectangularly spaced relation with each other around the central portion, with 2 ml of each of the above-mentioned culture liquors of the pathogenic fungi. In plots 3 and 4, two commercially available wetting agents for agricultural chemicals, namely, Rabicoto (trade name, a product of the firm Akebono Tsusho) and Petan V (trade name, a product of the firm Aguro.Kaneshou K.K.), respectively, were sprayed in a 100-fold dilution of the wetting agent onto the lawn grass-planted soil face, before spraying with the microbial product according to the present invention at a dosage of 10 or 50 g/m² and infecting with the pathogenic fungi. Each of the polycarbonate bottles were soaked in a sterilized water so as to cause the lawn grass therein to be completely immersed in the water. After five minutes, the water was discarded by tilting the bottle.

Six polycarbonate bottles with growing lawn grass were used for each experiment in each plot. Five portions in each bottle as explained above were infected with the pathogenic fungus and, hence, 6×5=30 portions were alloted for each experiment. The lawn grass was maintained in the dark at 3° C. for testing occurrence of snow blight disease. Over the lawn grass, a glass shell filled with 20 ml of sand was placed as a weight for simulating the condition of laid snow in the field pressing onto the grass. After 3 weeks, the bottles were taken out of the artificial climatic chamber and the lawn grass was inspected for the occurrence of snow blight at each infected portion to determine the number of portions suffered from the disease among the 30 infected portions (morbidity). The results are summarized in Table 19.

TABLE 19

| Experimental Plot | Dosage of microbial product | Infection with T. incarnata MAFF306126 | Morbidity (x/30) |
|---|---|---|---|
| 1: with only microb. prod. | 10 g/m² | 5 × 2 ml/Bottle | 21 |
|  | 50 g/m² | 5 × 2 ml/Bottle | 18 |
| 2: with 0.3% Na-CMC | 10 g/m² |  | 3 |
|  | 50 g/m² |  | 2 |
| 2: with 0.5% Na-CMC | 10 g/m² |  | 1 |
|  | 50 g/m² |  | 0 |
| 2: with 1.0% Na-CMC | 10 g/m² |  | 0 |
|  | 50 g/m² |  | 0 |
| 2: with 3.0% Na-CMC | 10 g/m² |  | 0 |
|  | 50 g/m² |  | 0 |
| 2: with 5.0% Na-CMC | 10 g/m² |  | 0 |
|  | 50 g/m² |  | 0 |
| 2: with 10.0% Na-CMC | 10 g/m² |  | 0 |
|  | 50 g/m² |  | 0 |
| 2: with 20.0% Na-CMC | 10 g/m² |  | 0 |
|  | 50 g/m² |  | 0 |
| 3: with Rabicoat | 10 g/m² |  | 17 |
|  | 50 g/m² |  | 14 |
| 4: with Petan V | 10 g/m² |  | 18 |
|  | 50 g/m² |  | 14 |

As seen in Table 19, an inhibitive effect on snow blights was attained by admixing a wetting agent, i.e. Na-CMC, to the microbial product for controlling snow blights according to the present invention, since any flooding off or washing away of the microbial product containing *Humicola grisea* var. *grisea* M6834 on the plant by a possible flooding by snow-thawing water will be prevented. It was also shown that the wetting agent for agricultural chemical is not suitable for the microbe of such kind. While it is seen that Na-carboxymethyl cellulose is effective even at a content of 10% by weight or higher, such a high content not only makes the microbial product according to the present invention inadaptable for the practival use in the economical point of view but also is wasteful and unnecessary.

EXAMPLE 13

In the Na-CMC-containing microbial product shown in the above Example, the influence of Na-CMC on the proliferation of *Humicoa grisea* var. *grisea* M6834 was tested. To each of the test products consisting of only the microbial product of Example 1 and of mixtures of microbial product of Example 1 with 0.5, 1.0, 5.0 and 10.0% of Na-CMC, respectively, a sterilized water was added so as to reach a water content of 50% by weight and the resulting mixtures were incubated at 3° C. for 5 days. It was confirmed that *Humicola grisea* var. *grisea* M6834 proliferates with increasing content of Na-CMC. Results are given in Table 20.

TABLE 20

| Na-CMC content (wt.-%) | Cell conc. (× 10⁴ CFU/g) | |
|---|---|---|
|  | test start | test end |
| — | 8.2 | 8.9 |
| 0.5 | 8.0 | 10.9 |
| 1.0 | 7.5 | 12.3 |
| 5.0 | 7.2 | 14.5 |
| 10.0 | 6.9 | 16.8 |

We claim:

1. A biologically pure culture of *Humicola grisea* var. *grisea* FERM BP-5452 wherein the said culture exhibits antagonism against the pathogenic fungi which cause snow mold diseases.

2. The culture as claimed in claim 1, wherein the pathogenic fungi are *Typhula incarnata, Typhula ishikariensis, Sclerotinia borealis, Fusarium nivale, Pythium paddicum, Pythium iwayamai, Pythium horinouchiensis* or *Pythium graminicola*.

3. The culture according to claim 1, wherein said culture exhibits antagonism also against the pathogenic fungi of plant diseases other than snow mold diseases.

4. The culture according to claim 1, wherein the pathogenic fungi are *Pythium ultimum, Pythium torulosum, Pythium vanteropoolii, Pythium aphanidermatum,* Rhizoctonia, *Pythium myriotylum, Carvularia geniculata, Carvularia lunata, Carvularia trifolii, Bipolaris sorokiniana, Fusarium avenaceam, Fusarium graminearum, Sclerotinia homoeocarpa* Bennet, *Pythium graminicola,* Subramaniam, *Curvularia geniculata* or *Gaeumannomyces graminis*.

5. A fungicidal composition comprising the culture according to claim 1 in admixture with an excipient.

6. The composition according to claim 5, whose moisture content is no more than 30% by weight.

7. The composition according to claim 5, containing at least 150,000 colony forming units of cells per gram of composition.

8. The composition according to claim 5, further comprising a wetting agent.

9. The composition according to claim 8, wherein the wetting agent is sodium carboxymethyl cellulose.

10. A method for controlling plant disease damage, comprising applying to plants the composition according to claim 5.

11. The method according to claim 10, wherein the composition is applied to the ground in which said plants grow, at a population of at least 1,000,000 colony forming units of cells per square meter of ground.

* * * * *